(12) United States Patent
Xie et al.

(10) Patent No.: US 11,802,869 B2
(45) Date of Patent: *Oct. 31, 2023

(54) MODULAR ASSAY READER DEVICE

(71) Applicant: Becton, Dickinson and Company, Franklin Lakes, NJ (US)

(72) Inventors: Tong Xie, San Jose, CA (US); Stephan Hengstler, Campbell, CA (US); Vincent C. Moyer, Los Gatos, CA (US); Benny Wing Hung Lai, Fremont, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/814,308

(22) Filed: Jul. 22, 2022

(65) Prior Publication Data

US 2022/0357321 A1 Nov. 10, 2022

Related U.S. Application Data

(63) Continuation of application No. 16/222,348, filed on Dec. 17, 2018, now Pat. No. 11,397,181, which is a
(Continued)

(51) Int. Cl.
*G01N 33/543* (2006.01)
*G16H 10/40* (2018.01)
(Continued)

(52) U.S. Cl.
CPC ......... *G01N 33/54388* (2021.08); *C12M 1/34* (2013.01); *G01N 21/01* (2013.01);
(Continued)

(58) Field of Classification Search
CPC ........... G01N 33/558; G01N 33/54386; G01N 21/01; G01N 35/00722; G01N 35/008471;
(Continued)

(56) References Cited

U.S. PATENT DOCUMENTS 6,136,610 A 10/2000 Polito et al.
6,440,066 B1 8/2002 Brady
(Continued)

FOREIGN PATENT DOCUMENTS

EP 2787352 A 10/2014
JP 2016507727 A 3/2016
(Continued)

OTHER PUBLICATIONS

IP Location Finder, "How to find Geolocation of an IP Address?" Nov. 1, 2010; downloaded from http://www.iplocation.net, 3 pages.
(Continued)

*Primary Examiner* — Gabriel I Garcia
(74) *Attorney, Agent, or Firm* — Knobbe, Martens, Olson & Bear LLP

(57) ABSTRACT

Certain aspects relate to systems and usage techniques for modular lateral flow assay reader devices that can receive a number of different modules having a barcode scanning input device and optional network connectivity capabilities. A barcode scanning module can provide a simple input method that reduces errors compared to manual data entry. A network connectivity module can enable transmission of test results over a public network for standardizing, tracking and electronically connecting test results from assay reader devices located throughout a network. Such devices can programmatically implement a simplified workflow whereby pressing a single button readies the device for imaging, analyzing, and data storage/transmission and, in
(Continued)

some implementations, configures the device to operate in one of a plurality of device operation modes.

20 Claims, 8 Drawing Sheets

Related U.S. Application Data continuation of application No. PCT/US2017/036810, filed on Jun. 9, 2017.

(60) Provisional application No. 62/393,575, filed on Sep. 12, 2016, provisional application No. 62/353,505, filed on Jun. 22, 2016.

(51) Int. Cl.
  *C12M 1/34* (2006.01)
  *G01N 21/01* (2006.01)
  *G01N 35/00* (2006.01)
  *G01R 1/20* (2006.01)
  *G06K 7/10* (2006.01)

(52) U.S. Cl.
  CPC . *G01N 35/00722* (2013.01); *G01N 35/00871* (2013.01); *G01R 1/20* (2013.01); *G06K 7/10* (2013.01); *G16H 10/40* (2018.01); *B01L 2300/021* (2013.01); *G01N 2035/00326* (2013.01); *G01N 2035/00752* (2013.01); *G01N 2035/00841* (2013.01); *G01N 2035/00881* (2013.01)

(58) Field of Classification Search
  CPC ... G01N 35/00881; G01N 2035/00326; G01N 2035/00752; G01N 2035/00841; G01N 2035/00881; G16H 1/40; C12M 1/34; G01R 1/20; G06K 7/10; B01L 2300/021
  USPC .......................................................... 382/128
  See application file for complete search history.

(56) References Cited

U.S. PATENT DOCUMENTS

| | | | |
|---|---|---|---|
| 7,027,931 B1 | 4/2006 | Jones et al. |
| 7,437,302 B2 | 10/2008 | Haskell et al. |
| 7,519,591 B2 | 4/2009 | Landi et al. |
| 7,575,558 B2 | 8/2009 | Boecker et al. |
| 7,651,841 B2 | 1/2010 | Song et al. |
| 7,890,748 B1 | 2/2011 | Wyatt |
| 8,007,999 B2 | 8/2011 | Holmes et al. |
| 8,046,175 B2 | 10/2011 | Kuo et al. |
| 8,106,780 B2 | 1/2012 | Goodnow et al. |
| 8,115,635 B2 | 2/2012 | Goodnow et al. |
| 8,138,909 B2 | 3/2012 | Lewington et al. |
| 8,223,021 B2 | 7/2012 | Goodnow et al. |
| 8,257,654 B2 | 9/2012 | Maus et al. |
| 8,260,392 B2 | 9/2012 | Say et al. |
| 8,358,210 B2 | 1/2013 | Goodnow et al. |
| 8,428,966 B2 | 4/2013 | Green, III et al. |
| 8,606,593 B1 | 12/2013 | Green, III et al. |
| 8,669,047 B2 | 3/2014 | Holmes et al. |
| 8,737,971 B2 | 5/2014 | Van Rooyen et al. |
| 8,773,258 B2 | 7/2014 | Vosch et al. |
| 9,310,300 B2 | 4/2016 | Alt et al. |
| 9,459,200 B2 | 10/2016 | Dupoteau et al. |
| 9,524,372 B2 | 12/2016 | Hengstler et al. |
| 9,715,579 B2 | 7/2017 | Hengstler et al. |
| 9,792,809 B2 | 10/2017 | Dupoteau |
| 9,795,331 B2 | 10/2017 | Stafford |
| 10,180,417 B2 | 1/2019 | Hengstler et al. |
| 10,309,954 B2 | 6/2019 | Adelman |
| 10,458,972 B2 | 10/2019 | Hengstler et al. |
| 10,706,966 B2 | 7/2020 | Hengstler et al. |
| 10,976,298 B2 | 4/2021 | Hengstler et al. |
| 11,152,116 B2 | 10/2021 | Hengstler et al. |
| 11,253,852 B2 | 2/2022 | Low et al. |
| 11,397,181 B2* | 7/2022 | Xie ............... G01N 33/54386 |
| 2002/0059030 A1 | 5/2002 | Otworth et al. |
| 2003/0073931 A1 | 4/2003 | Boecker et al. |
| 2004/0167464 A1 | 8/2004 | Ireland et al. |
| 2004/0249999 A1 | 12/2004 | Connolly et al. |
| 2006/0240568 A1 | 10/2006 | Petruno et al. |
| 2007/0016381 A1 | 1/2007 | Kamath et al. |
| 2007/0081920 A1 | 4/2007 | Murphy et al. |
| 2007/0184847 A1 | 8/2007 | Hansen et al. |
| 2008/0024294 A1 | 1/2008 | Mazar |
| 2008/0240983 A1 | 10/2008 | Harris |
| 2009/0013311 A1 | 1/2009 | Ooba et al. |
| 2009/0058635 A1 | 3/2009 | LaLonde et al. |
| 2009/0058636 A1 | 3/2009 | Gaskill et al. |
| 2009/0132204 A1 | 5/2009 | Bodlaender et al. |
| 2009/0155921 A1 | 6/2009 | Lu et al. |
| 2009/0163832 A1 | 6/2009 | Sunderani |
| 2009/0192410 A1 | 7/2009 | Freeman et al. |
| 2009/0271066 A1 | 10/2009 | Underdal et al. |
| 2009/0292340 A1 | 11/2009 | Mass et al. |
| 2010/0045789 A1 | 2/2010 | Fleming et al. |
| 2010/0159599 A1 | 6/2010 | Song et al. |
| 2010/0185711 A1 | 7/2010 | Subramaniam |
| 2010/0257027 A1 | 10/2010 | Greenberg et al. |
| 2010/0267049 A1 | 10/2010 | Rutter et al. |
| 2011/0053121 A1 | 3/2011 | Heaton |
| 2011/0230743 A1 | 9/2011 | Inciardi et al. |
| 2011/0291643 A1 | 12/2011 | Ravindran et al. |
| 2011/0293153 A1 | 12/2011 | Plickert et al. |
| 2011/0295078 A1 | 12/2011 | Reid et al. |
| 2011/0295091 A1 | 12/2011 | Azer et al. |
| 2012/0100557 A1 | 4/2012 | Fox et al. |
| 2012/0112908 A1 | 5/2012 | Prykari et al. |
| 2012/0232367 A1 | 9/2012 | Allegri et al. |
| 2013/0018668 A1 | 1/2013 | Goldberg et al. |
| 2013/0066562 A1 | 3/2013 | Hengstler et al. |
| 2013/0066563 A1 | 3/2013 | Hengstler et al. |
| 2013/0184188 A1 | 7/2013 | Ewart et al. |
| 2013/0200140 A1 | 8/2013 | Kawabata et al. |
| 2013/0203620 A1 | 8/2013 | Glezer et al. |
| 2013/0210163 A1 | 8/2013 | Hopwood et al. |
| 2013/0281310 A1 | 10/2013 | Weidemaier et al. |
| 2014/0228225 A1 | 8/2014 | Triener et al. |
| 2014/0260568 A1 | 9/2014 | Modzelewski et al. |
| 2014/0316732 A1 | 10/2014 | Dupoteau |
| 2015/0323461 A1 | 11/2015 | Chan et al. |
| 2017/0175169 A1 | 6/2017 | Lee |
| 2018/0137940 A1 | 5/2018 | Hengstler et al. |
| 2019/0229907 A1* | 7/2019 | Nicolson ............... H04L 63/168 |
| 2021/0372985 A1 | 12/2021 | Hengstler et al. |
| 2022/0165409 A1 | 5/2022 | Hengstler et al. |

FOREIGN PATENT DOCUMENTS

| | | | |
|---|---|---|---|
| WO | WO 2013/052318 A1 | 4/2013 |
| WO | WO 2011/115028 A1 | 6/2013 |
| WO | WO 2014/159672 A1 | 10/2014 |
| WO | WO 2015/008094 A1 | 1/2015 |

OTHER PUBLICATIONS

IP Location, How Do I find a geographical location from an IP Address?, http://www.iplocation.net, Nov. 15, 2010; 2 pages.
Martinelli, Nicole, "How Hospitals are Using the iPad", downloaded from http://www.cultofmac/com/64565/how-hospitals-are-using-the-ipad; Oct. 19, 2010, 4 pages.
The Free Dictionary, "Definition of Protocol", downloaded from http://www.thefreedictionary.com/p/protocol; Jul. 2014, 3 pages.
TÜV (Technischer Überwachungs Verein—Süd), "In vitro diagnostic devices directive—Understanding", (98/79/EC) 2008, in 9 pages.
International Search Report and Written Opinion dated Aug. 25, 2017 in International Application No. PCT/US2017/036810.

* cited by examiner

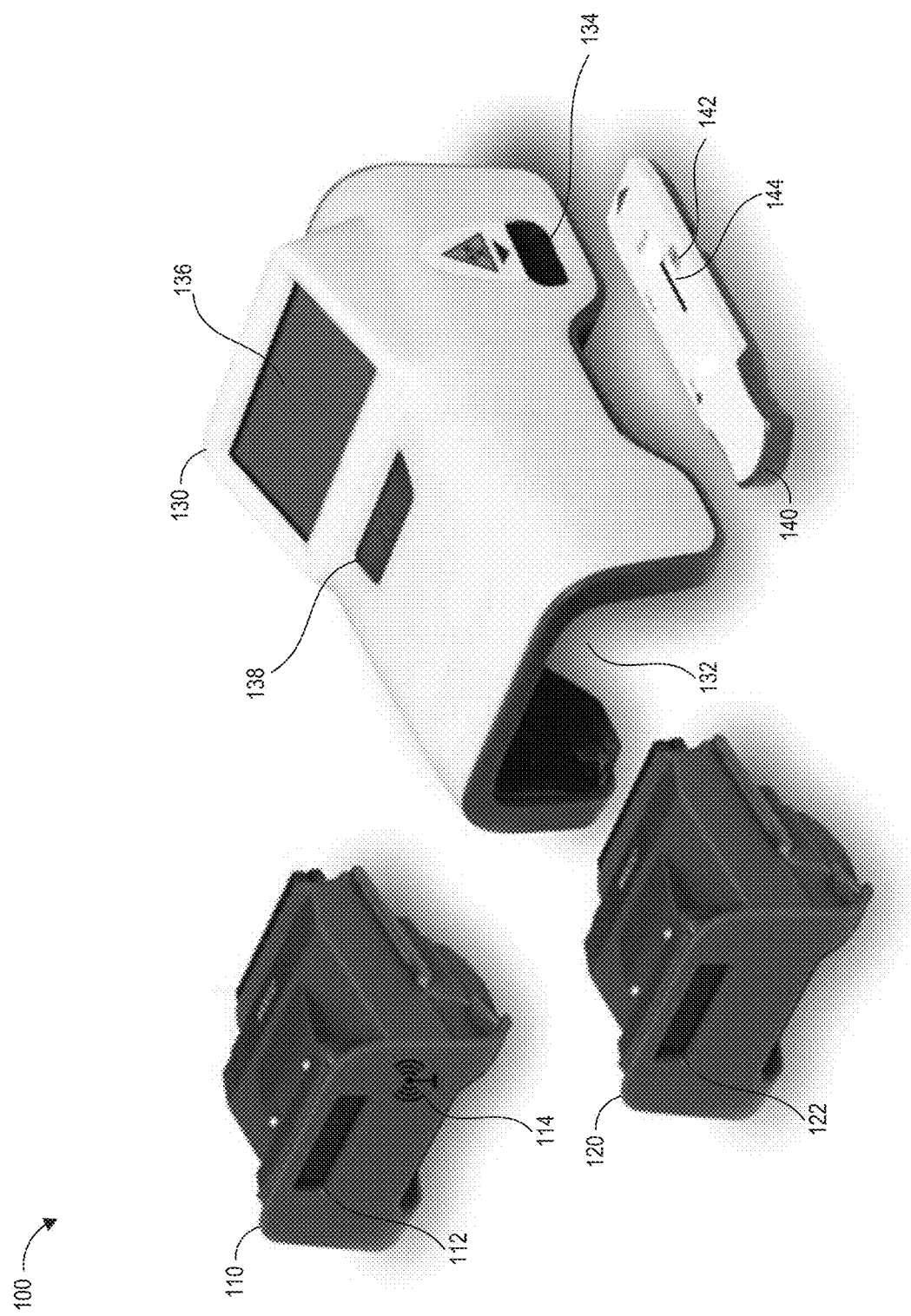

| SCAN CONFIG BARCODE | S/N: XXXXXXXXXXXX<br>Expiration: DD-MMM-YYYY<br>Tests Remain: XXXX<br>OID: Yes  SID: Yes  LOT: No<br>Language: English<br>FW Ver: X.XX | SCAN OPERATOR ID |
|---|---|---|
| SPECIMEN ID SCAN ENABLED | KIT LOT NUMBER SCAN ENABLED | OPERATOR ID:<br>XXXXXXXXXXXXXXXX<br>SCAN SPECIMEN ID |
| SPECIMEN ID SCAN DISABLED | KIT LOT NUMBER SCAN DISABLED | |
| OPERATOR ID SCAN ENABLED | | |
| OPERATOR ID SCAN DISABLED | | |

FIG. 6

MODULAR ASSAY READER DEVICE

CROSS-REFERENCE TO RELATED APPLICATIONS

This application is a continuation of U.S. patent application Ser. No. 16/222,348, filed Dec. 17, 2018 and scheduled to issue on Jul. 26, 2022 as U.S. Pat. No. 11,397,181, which is a continuation of PCT Application No. PCT/US2017/036810, filed Jun. 9, 2017, which claims the benefit of U.S. Provisional Patent Application No. 62/393,575, filed on Sep. 12, 2016, entitled "MODULAR ASSAY READER DEVICE," and U.S. Provisional Patent Application No. 62/353,505, filed on Jun. 22, 2016, entitled "MODULAR ASSAY READER DEVICE." Each of the above applications is hereby incorporated by reference in its entirety.

TECHNICAL FIELD

The systems and methods disclosed herein are directed to medical testing, and, more particularly, to lateral flow assay techniques and devices.

BACKGROUND

In patient care, immunoassay technology provides simple and relatively quick means for determining the presence of analytes in a subject sample. Analytes are substances of interest or clinical significance that may be present in biological or non-biological fluids. The analytes can include antibodies, antigens, drugs, or hormones.

The analyte of interest is generally detected by reaction with a capture agent, which yields a device more easily detected and measured than the original analyte. Detection methods can include a change in absorbance, a change in color, change in fluorescence, change in luminescence, change in electrical potential at a surface, change in other optical properties, or any other easily measured physical property indicating the presence or absence of an analyte in a sample.

SUMMARY

Immunoassay devices play an important role in areas such as clinical chemistry and have been made portable for use in the field. Assays are routinely performed to detect the presence of particular analytes that are present when a human or non-human subject has a particular disease or condition. For example, an assay as described herein can be used to detect whether a patient has flu A, flu B, RSV, group A strep, or another illness, is experiencing ovulation or pregnancy, or has a particular drug or chemical compound in their body, to name a few examples.

Such assays and assay reader devices are used by skilled clinicians and laypersons alike. Accordingly, an assay reader device according to the present disclosure is designed to be simple and reliable, for example by including a module for simple barcode scan input of any needed additional information and by minimizing a number of steps required for the user to perform between sample application and result notification. The barcode scan input can provide for a high level of traceability and compliance by allowing clinics, laboratories, and the like to implement custom test result documentation standards. Some examples can enforce compliance with such standards at the reader level, for example by pre-configuring the readers to require input of designated types of information before transmitting results. As another example, communications between the reader and a centralized database can be used to ascertain whether transmitted test data complies with such standards and, if not, to send instructions back to the reader device to prompt a user for any missing information. Further, such assays and assay reader devices can be used in a variety of contexts, both inside and outside of the clinical setting. Accordingly, an assay reader device according to the present disclosure can include a module providing network connectivity capabilities for providing test results to one or more centralized databases.

Accordingly, one aspect relates to a diagnostic test device comprising an optical sensor positioned to detect changes in optical characteristics of an assay following application of a biological sample to the assay, the optical sensor configured to generate a signal indicating the detected changes in optical characteristics of the assay; a module interface comprising a bay configured to receive and lockingly engage a connected module of a plurality of interchangeable modules, a first signal path configured to identify characteristics of the connected module, the characteristics indicative of presence of a barcode scanner in the connected module and connectivity capabilities of the connected module, and a second signal path configured to receive barcode data from the connected module, the barcode data representing a barcode imaged by the connected module; at least one processor; and a memory having instructions stored thereon that configure the at least one processor to determine a test result based at least partly on the signal generated by the optical sensor, identify the barcode as an identification information barcode, determine identification information based on the barcode data, determine the connectivity capabilities of the connected module, in response to determining that the connected module has connectivity capabilities with a remote storage device, automatically send the test result in association with the identification information to the remote storage device, and in response to determining that the connected module does not have connectivity capabilities with a remote storage device, automatically store the test result in association with the identification information in the memory.

Some embodiments can further comprise an additional optical sensor positioned to detect additional information on the assay or a cartridge holding the assay, wherein the at least one processor is configured to use the additional information to establish operating parameters of the diagnostic test device. Some embodiments can further comprise an additional optical sensor positioned to detect additional information on the assay or a cartridge holding the assay, wherein the at least one processor is configured to store the additional information in association with the test result.

Some embodiments can further comprise the connected module. The connected module can comprise the barcode scanner. The connected module can comprise a cellular modem configured to provide the connectivity capabilities. The connected module can comprise an information element, wherein the at least one processor is configured to retrieve, via the first signal path, module information from the information element and determine the connectivity capabilities of the connected module based on the module information.

Another aspect relates to a non-transitory computer-readable media configured with computer-executable instructions that, when executed, cause a hardware processor: to identify characteristics of a connected module inserted into a bay of an assay reader device, the characteristics indicative of presence of a barcode scanner in the connected module and connectivity capabilities of the connected module; receive assay image data from an assay reading image sensor of the assay reader device, the assay image data representing detected changes in optical characteristics of an assay inserted into or positioned adjacent to the assay reader device; determine a test result based at least partly on analyzing the assay image data; determine, based on the identified characteristics, the connectivity capabilities of the connected module; in response to determining that the connected module has connectivity capabilities with a remote storage device physically separated from the assay reader device, automatically send the test result to the remote storage device; and in response to determining that the connected module does not have connectivity capabilities with a remote storage device, automatically store the test result in a memory of the assay reader device.

The non-transitory computer-readable media can further have stored thereon instructions that, when executed, cause the hardware processor to receive barcode image data from the connected module representing at least one barcode; identify, based on analysis of the barcode image data, the at least one barcode as an instruction barcode; and retrieve instructions associated with the instruction barcode. The non-transitory computer-readable media can further have stored thereon instructions that, when executed, cause the hardware processor to determine the test result based at least partly on the instructions. The non-transitory computer-readable media can further have stored thereon instructions that, when executed, cause the hardware processor to instruct the assay reading image sensor to obtain the assay image data at a predetermined timing after insertion of the assay into the assay reader device based at least partly on the instructions.

The non-transitory computer-readable media can further have stored thereon instructions that, when executed, cause the hardware processor to receive barcode image data from the connected module representing at least one barcode; identify, based on analysis of the barcode image data, the at least one barcode as an identification barcode; determine information represented by the identification barcode; in response to determining that the connected module has connectivity capabilities with a remote storage device physically separated from the assay reader device, automatically send the information represented by the identification barcode with the test result to the remote storage device; and in response to determining that the connected module does not have connectivity capabilities with a remote storage device, automatically store the information represented by the identification barcode with the test result in a memory of the assay reader device.

Another aspect relates to a diagnostic testing process comprising, by one or more hardware processors: identifying characteristics of a connected module inserted into a bay of an assay reader device, the characteristics indicative of presence of a barcode scanner in the connected module and connectivity capabilities of the connected module; receiving assay image data from an assay reading image sensor of the assay reader device, the assay image data representing detected changes in optical characteristics of an assay inserted into or positioned adjacent to the assay reader device; determining a test result based at least partly on analyzing the assay image data; determining, based on the identified characteristics, the connectivity capabilities of the connected module; in response to determining that the connected module has connectivity capabilities with a remote storage device physically separated from the assay reader device, automatically sending the test result to the remote storage device; and in response to determining that the connected module does not have connectivity capabilities with a remote storage device, automatically storing the test result in a memory of the assay reader device.

The process can further comprise receiving barcode image data from the connected module representing at least one barcode; identifying, based on analysis of the barcode image data, the at least one barcode as an instruction barcode; and retrieving instructions associated with the instruction barcode. The process can further comprise determining the test result based at least partly on the instructions. The process can further comprise instructing the assay reading image sensor to obtain the assay image data at a predetermined timing after insertion of the assay into the assay reader device based at least partly on the instructions.

The process can further comprise receiving barcode image data from the connected module representing at least one barcode; identifying, based on analysis of the barcode image data, the at least one barcode as an identification barcode; and determining information represented by the identification barcode. The process can further comprise, in response to determining that the connected module has connectivity capabilities with a remote storage device physically separated from the assay reader device, automatically sending the information represented by the identification barcode with the test result to the remote storage device; and in response to determining that the connected module does not have connectivity capabilities with a remote storage device, automatically storing the information represented by the identification barcode with the test result in a memory of the assay reader device. The process can further comprise, in response to determining that the connected module has connectivity capabilities with a remote storage device physically separated from the assay reader device, automatically sending instructions to route the test result from the remote storage device to another remote storage device, the another remote storage device identified based on the information represented by the identification barcode. The process can further comprise, in response to determining that the connected module has connectivity capabilities with a remote storage device physically separated from the assay reader device, automatically sending the test result to the personal computing device of a clinician, the clinician identified based on the information represented by the identification barcode.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 1A illustrates an example set of components for an assay reader system.

FIG. 6 illustrates various examples of display text that can be presented to an operator on a display screen of an assay reader device as described herein.

DETAILED DESCRIPTION

Introduction

Figure 1B:
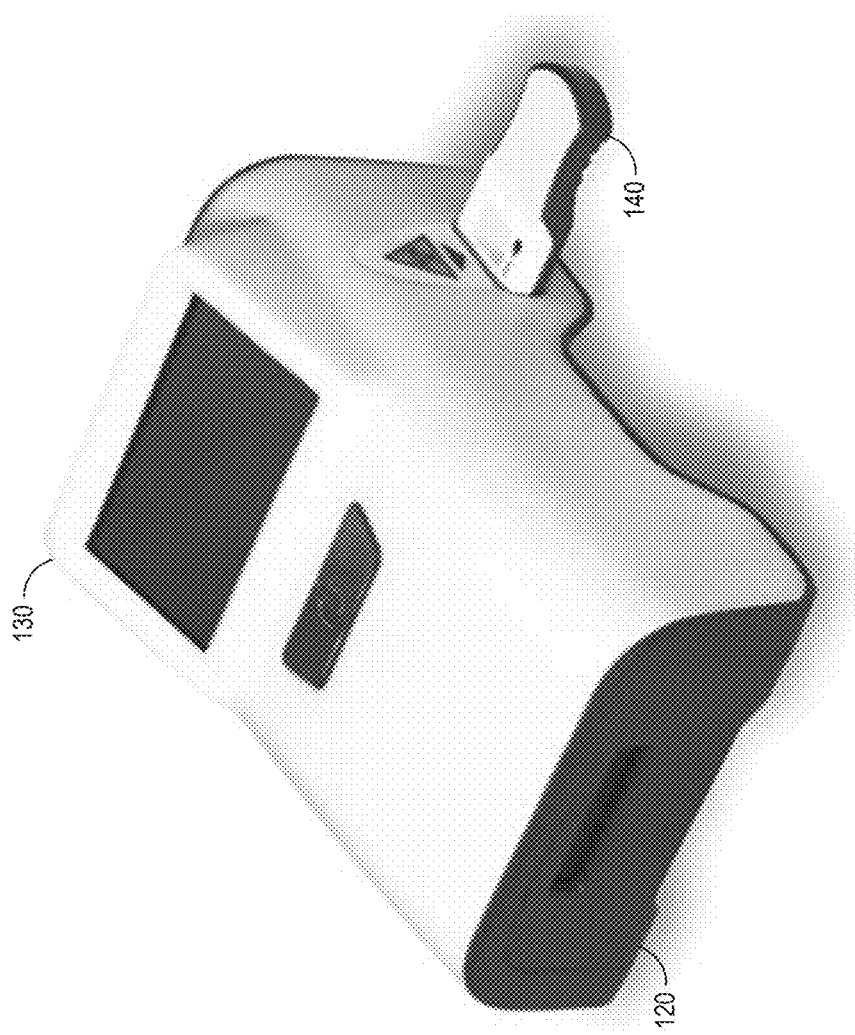
FIG. 1B illustrates an example assembled reader and module of the assay reader system of FIG. 1A.

Embodiments of the disclosure relate to systems and techniques for modular assay reader devices that can receive a number of different modules having a barcode scanning input device and optional network connectivity capabilities. Embodiments of the reader devices can be portable, for example relatively small and light with an option to run off of stored power. The disclosed reader devices can be used in hospitals, clinics, doctors' offices, and other patient care facilities to enable rapid detection and identification of numerous types of biological conditions, such as the presence of infection antibodies. A network connectivity module can enable standardizing, tracking and electronically connecting test results from reader devices located throughout a network for improved patient care.

One type of reader device is configured to read or otherwise analyze lateral flow assays, which can test for a wide variety of medical and environmental conditions or compounds. For example, lateral flow tests can rely on a form of immunoassay in which the test sample flows along a solid substrate via capillary action. Lateral flow assay reader devices can read lateral flow assay strips to detect the existence of a hormone, metabolite, toxin, or pathogen-derived antigen. This reading can be accomplished with the use of a detector containing one or more sensing elements, such as but not limited to a PIN detector, a linear array detector, a CMOS imager, and a CCD-based imaging device, which is configured to detect the presence or absence of a line on the lateral flow assay based on the presence or absence of a visual line on the assay. Some tests, implemented by assay reader devices, are designed to make a quantitative determination, but in many circumstances the tests are designed to return or indicate a positive/negative qualitative indication. Examples of assays that enable such qualitative analysis include blood typing, most types of urinalysis, pregnancy tests, and HIV/AIDS tests. The assay reader device can identify a result of such tests by autonomously following a pre-programmed decision-making process or rule. In addition to reader devices configured to analyze lateral flow assays, implementations of diagnostic reader devices described herein can analyze other types of assays, such as but not limited to molecular assays, and provide a diagnostic test result.

The assay reader device can be a single-step device wherein the user need only apply the sample prior to viewing the result and optionally having the result transmitted to appropriate hospital, laboratory, or medical record databases. Such a single-step device can obviate the necessity of performing complicated and time consuming processing steps that may introduce errors in the end result. For example, a user may press a single button on the assay reader device to power the device on. Thereafter, insertion of a sample cartridge into the device can automatically activate a reading process to determine and display a test result based on the sample cartridge without further user input. In some embodiments having network connectivity capabilities, the determined test result can additionally be automatically sent without requiring further user input to a remote storage device, for example to centralized database and then from the centralized database to a designated clinician or another database, for example a Hospital Information System (HIS), Laboratory Information System (LIS), or a database maintained by a public health agency like the CDC, FDA, and WHO. In some embodiments having network connectivity capabilities, the determined test result can be sent directly to the designated clinician or database. As used herein, a remote storage device can be the centralized database, HIS, LIS, public health agency database, device of a designated clinician, or any other data storage not physically coupled to the assay reader device.

The disclosed portable assay devices can include a base assay analyzer, such a base assay reader device, having a bay for receiving a number of different modules. One module can include a barcode scanner for use in user input of any needed additional information, for example patient identification information, test type, device operation mode, sample information, and any other additional test or patient information pertinent to the test performed by the IVD device. In some embodiments device operation mode can be set via a number or pattern of clicks of a single button of the base assay analyzer. Another module can include the barcode scanner and additionally a network connection element. Such a modular design approach allows the assay reader device to expand its functionalities, for example to provide barcode scanning and wireless connectivity, while maintain its portability and cost advantage. The selection of different modules provides the user with the flexibility to decide the best functional capabilities necessary for their own settings or applications. The module can be an optional accessory to the base assay analyzer, and the base assay analyzer can function without a module inserted to read inserted assays, for example lateral flow assay test strips. A module can be swapped among analyzers. Once inserted, the module can become an integral part of the analyzer.

As indicated above, one of the modules can include both a barcode reader and a communication component for network connectivity, for example via a wireless connection such as a cellular modem, satellite connection, or Wi-Fi, or via a wired connection. When such a module is inserted into a bay of the assay reader device and in electronic communication with a memory and/or processor of the device, the assay reader device becomes capable of sending or uploading data to a remote repository via a network. As such, the test data of such assay reader devices can be stored and analyzed, alone or in the aggregate, by remote devices or personnel. A module having a cellular or satellite modem provides a built-in mechanism for accessing publicly available networks, such as telephone or cellular networks, to enable direct communication by the assay reader device with network elements or other IVD devices to enable electronic test result transmission, storage, analysis and/or dissemination without requiring separate intervention or action by the user of the device. For example, in some cases, the electronic test result transmission, storage, analysis and/or dissemination occurs automatically upon a patient sample being analyzed by the assay reader device. In another example, the electronic test result transmission, storage, analysis and/or dissemination occurs immediately upon a patient sample being analyzed by the assay reader device. In some embodiments the module can provide connection to a cloud database, for example a server-based data store. The cloud based connectivity module can enable ubiquitous connectivity of assay reader devices without the need for a localized network infrastructure.

Using the barcode scanner, device users can customize an assay reader device to perform various workflows best fit to their environment and compliance requirements. This barcode scan approach offers a simple and error-free way for the end-user to customize a diagnostic device. For example, barcodes can be scanned to set a device operation mode or to specify required types of information to comply with requirements, such healthcare organization standards, compliance standards, documentation standards, reporting standards, or any other requirement applicable to the testing environment.

In some embodiments device operation mode can additionally or alternatively be set via a number or pattern of clicks of a single button of the base assay analyzer. For example, in some implementations a single press of the button can power on the base assay analyzer and set the analyzer to a default operation mode, and the device can implement the default operation mode upon insertion of a cartridge. A double click of the button can initiate an alternate operation mode that is different than the default operation mode. Other numbers or patterns of pressing the single button by a user can provide instructions to the processor of the device regarding a desired operation mode. Embodiments of a base assay analyzer are described herein with reference to a single button, but other features allowing a user to select and switch between device operation modes are possible (such as but not limited to a single switch, knob, lever, or handle).

One example of a device operation mode is end-point read mode. In the end-point read mode, the user prepares and incubates the assay outside of the base assay analyzer and tracks the development time of the assay. For example, a flu assay can have a development time of 10 minutes, so the user would apply the specimen to the assay and wait for 10 minutes. At the end of the 10 minutes the user would insert the assay into the base assay analyzer to obtain a test result. Accordingly, when operating in end-point read mode the base assay analyzer can provide instructions, for example audibly or on a visual display, that instruct a user to wait for a predetermined time after applying a sample to an assay before inserting the assay in the base assay analyzer. In other embodiments, when operating in end-point read mode the base assay analyzer may not display any instructions but may simply read an assay upon insertion into the base assay analyzer. Upon insertion of the assay into the base assay analyzer, an optical reader of the device can collect image data representing the assay for analysis in determining a result of the assay. In some embodiments end-point read mode can be the default operation mode of a base assay analyzer.

Another example of a device operation mode is walkaway mode. Accordingly, when operating in walkaway mode the base assay analyzer can provide instructions for the user to insert the assay immediately after or during application of the sample. In the walkaway mode according to one embodiment, the user can apply the specimen to the assay and immediately insert the assay into the base assay analyzer. The assay will develop inside the base assay analyzer and the base assay analyzer can keep track of the time elapsed since insertion of the assay. At the end of the predetermined development time, the base assay analyzer can collect image data representing the assay, analyze the image data to determine a test result, and report the test result to the user. The assay development time can be unique to each test, for example a flu assay development time can be 10 minutes and a strep assay development time can be 5 minutes. In some embodiments walkaway mode can be set by double-clicking the single button of the base assay analyzer. Further input can indicate the assay development time to the reader device. For example, a barcode scanned by the barcode reader of the inserted module, or a barcode provided on the assay or on a cartridge used to hold the assay, can indicate to the device a type of assay that is inserted and a development time for that assay. Based upon the type of assay, the base assay analyzer can wait for the predetermined amount of time after sample application and insertion before collecting image data representing the assay.

There are many advantages associated with the ability of a user to select and switch between device operation modes in implementations of base assay analyzers described herein. The endpoint read mode can be convenient in large laboratories or medical practice facilities where personnel typically batch process a number of tests. The walkaway mode can be useful when a single test is being performed, or when the end user does not want to have to track the assay development time (or is not knowledgeable or not trained on how to track the assay development time accurately). The walkaway mode can advantageously reduce or eliminate the occurrence of incorrect test results due to an assay being inserted and imaged too quickly (too soon before the development time of the assay has elapsed) or too slowly (too long after the development time of the assay has elapsed). Further, in walkaway mode the assay reader can operate to capture multiple images of the assay at predetermined time intervals, for example when a kinetic graph of the assay readings is desired.

One embodiment of the disclosed base assay analyzer, such as a base assay reader device described in detail below, includes only a single button on its exterior housing, such as a single power button that powers the base assay analyzer off and on. Embodiments of the disclosed base assay analyzer also implement two different device operation modes (although more than two device operation modes are possible). In order to enable the end user to select and switch between the two device operation modes, the base assay analyzer can include instructions to implement a double-click function on the power button. After receiving input of a single press of the button to power on the device, insertion of an assay cartridge can automatically trigger end-point read mode. When the processor of the device receives input from a user double clicking the power button, this can initiate the stored instructions to implement the walkaway mode. This double click functionality offers a simple and intuitive way for the end user to switch between different operation modes of the base assay analyzer. The double click functionality also enables the user to configure the device in real time to operate in the walkaway mode without requiring any additional configuration steps or additional programming of the base assay analyzer by the user. It will be appreciated that the base assay analyzer can be provided with instructions to recognize other click modes instead of or in addition to the double click to trigger secondary (non-default) device operation modes, for example to recognize a user pressing the button any predetermined number of times, pressing the button in a predetermined pattern, and/or pressing and holding the button for a predetermined length of time.

Other examples of barcode uses include, as described above, providing additional data for association with test result data, including patient identification information, test type, device operation mode, sample information, and any other additional test or patient information pertinent to the test performed by the IVD device. Some barcodes can unlock device functions. Some barcodes can provide or update various types of information the device uses to analyze an assay, determine a test result, or perform a function. For example, a scanned barcode can provide to the reader device assay or reader calibration information that is useful or necessary to perform the test. In embodiments in which the device does not have wireless network connectivity, test results can be stored in a memory of the device, and in order to access the stored test results a user can scan a password barcode using the barcode scanner.

Although the disclosed devices are typically described herein as assay reader devices, it will be appreciated that the modular system design and network connectivity aspects described herein can be implemented in any suitable in-vitro diagnostic device. For example, features described herein can be implemented in reader devices that analyze other types of assays, such as but not limited to molecular assays, and provide a diagnostic test result.

Various embodiments will be described below in conjunction with the drawings for purposes of illustration. It should be appreciated that many other implementations of the disclosed concepts are possible, and various advantages can be achieved with the disclosed implementations.

Overview of Example Assay Reader Devices and Operations

FIG. 1A illustrates an example set of components for an assay reader system 100. The set of components includes a barcode module 120 and a barcode and connectivity module 110 that can be lockingly inserted into a bay 132 of a base assay reader device 130, and the set of components further includes a cartridge 140 for holding an assay 144 for insertion into the base assay reader device 130. FIG. 1B illustrates an example assembly of the base assay reader device 130 and barcode module 120 with the cartridge 140 inserted into a cartridge receiving aperture 134 of the reader 130. The components of FIGS. 1A and 1B will be discussed together in the discussion below.

Base assay reader device 130 includes a bay 132 for lockingly and optionally releasably receiving one of a number of different modules, a cartridge receiving aperture 134, a display 136, and a single button 138. The bay 132 can include both mechanical features for lockingly mating with corresponding mechanical features of an inserted module as well as electrical features for establishing electronic data communications with components of the inserted module. Base assay reader device 130 can be capable of providing basic assay analysis and data storage features without any inserted module, and an inserted module can be selected and inserted to expand upon the basic features. In embodiments in which no module is inserted, a cover can be provided over the opening of the bay 132. For example, the device 130 may be originally provided with the cover, and the cover can be removed to insert one of the interchangeable modules.

The cartridge receiving aperture 134 can be sized and shaped to align a test region of an assay with a detector or detector array provided within the device 130 when the assay is inserted through the cartridge receiving aperture 134. For example, if the assay is lateral flow assay test strip the test region can include one or more of a control zone and a test zone having immobilized compounds that are capable of specifically binding the target analyte. The detector can implement adaptive read technology to improve specificity of test results and to reduce false-positive results by compensating for background and non-specific binding. The base assay reader device 130 can be configured for fast and accurate assay performance, for example as a digital immunoassay configured for detecting Flu A+B, RSV and Group A Strep in 10 minutes or less. This can aid in rapid diagnosis and facilitate a test-and-act-approach while the patient is in the office.

Display 136 of base assay reader device 130 can be an LED, LCD, OLED, or other suitable digital display and can implement touch-sensitive technologies in some embodiments. Button 138 can be a mechanical button for powering on the base assay reader device 130. As described above, the device can include instructions to recognize a pattern of presses of the single button 138 in order to select a device operation mode. As discussed in more detail below, button 138 can provide users with secure, one-touch wireless electronic medical record synchronization when a connectivity module is inserted into the bay 132 of device. For example, a single press (or pattern of presses) of the simple one-touch button can ready the base assay reader device 130 for use, store test result data to the device memory, and transfer the test result to a patient electronic medical record through the connectivity module. Other embodiments of the device 130 may power on and be readied for use automatically when plugged in or otherwise powered and thus button 138 may be omitted. In other embodiments, multiple buttons can be provided on the device 130. The assay reader device can further include a processor and at least one memory, as discussed in more detail below. Base assay reader device 130 can be data storage and printing enabled.

Barcode module 120 includes a barcode scanner 122. Barcode scanner 122 can include one or more photodetectors and optionally light emitting devices for reading barcodes. For example, one implementation of barcode scanner 122 can include a light source, a lens for focusing the light source onto an object, and a light sensor for receiving light reflected off of the object and translating the received light into electrical signals. Some implementations of a sensor of barcode scanner 122 can include an array of many tiny light sensors such that a voltage pattern generated by the array is substantially identical to the pattern in a barcode. The barcode scanner 122 can also include decoder circuitry or software for analyzing the image data provided by the sensor, identifying a barcode pattern in the image data, determining content associated with the barcode pattern, and outputting the content, for example to a processor of the assay reader device. Barcode module 120 can further include mechanical features for lockingly engaging corresponding features within the bay 132 of the base assay reader device 130 and electronic features for establishing electronic data communications with components of the base assay reader device 130.

Though not illustrated, barcode module 120 can include an information element, for example a memory device or other active or passive electrical component. A passive information element can include transistor networks, PROMs, ROMs, EPROM or other programmable memory, EEPROM or other reprogrammable memory, gate arrays and PLAs to name a few examples. The information element can function to identify the capabilities of barcode module 120 to the assay reader and/or to authenticate the barcode scanning capabilities of barcode module 120 as a module from a specific source or manufacturer.

The barcode module 120 can ensure a high level of traceability and quality control via a customizable documentation functionality, data storage/download, and printing capability, while reducing manual transcription and risk of errors. As used herein, traceability can refer to the ability to verify the location, time, personnel, patient, or other information associated with a test performed using a reader device by means of documented information. The documented information can be advantageously accessed by numerous entities in a number of ways described herein. As described above, the barcode scanner can be used to enter test-related data, change device settings, unlock data access or other features, or to change the device mode. Test-related data can include user ID, clinician or test administrator ID, specimen ID, and test kit lot and/or expiration, among other test-related information described herein. Multiple operating modes for the assay reader device provide a flexible workflow implemented via barcode scanning.

With respect to traceability, a hospital, clinic, laboratory, or other healthcare organization can have internal standards specifying type(s) of information that are required to be recorded about each test performed in order for the test results to be compliant with applicable regulations. The barcode scanner can enable a clinician administering a test to input the required information by scanning a barcode. In some implementations, a barcode scanning module can be pre-programmed to output a listing of the required types of information associated with each test, or to output a prompt to a user to input any required information that has not been scanned before the test results are sent for storage. In some implementations, a barcode scanning module with connectivity functionality can communicate with a centralized database to provide a listing of the required types of information. The required types of information can be communicated wirelessly from the centralized database to the base assay reader device and displayed to the user. The user can input the required types of information by using the barcode scanning module to scan one of a plurality of available barcodes provided to the user. Once the barcodes associated with the required types of information have been scanned, the test result can be associated with the inputted information and sent securely, and in some cases automatically and/or wirelessly, to a laboratory information system and/or electronic medical record. The test result transmitted to the laboratory information system and/or electronic medical record is thus seamlessly and automatically associated with information (such as but not limited to user ID, clinician or test administrator ID, specimen ID, and test kit lot and/or expiration), significantly enhancing traceability of test results obtained using methods and systems described herein.

In some embodiments, a base assay reader device can allow the end-user to configure preset functions such as whether to require a patient ID barcode scan or Operator ID barcode scan at the start of each test. The configuration of these preset functions can be accomplished by scanning a configuration barcode that, once decoded by the device, includes instructions for the preset function scanning configuration. In one implementation, a healthcare facility administrator can initially select, from a set of printed barcodes, one or more barcodes corresponding to the types of information required by the administrator's desired configuration for a particular reader device; subsequent to this initial configuration selection, a user in the healthcare facility using the particular reader device can scan the appropriate barcodes to input information corresponding to the pre-selected functions of the reader device. The reader device can transmit all available information related to the test to a centralized server, for example via a connectivity module or a wired connection to another computing device. In one implementation, compliance may not be enforced at the reader level, and if the end user provided patient ID via a barcode scan then this information will be transmitted with the test result, otherwise the patient ID fields will be left blank. Other implementations can prompt the end user for the missing information. Local data storage, download, and print options can help to ensure compliance and traceability if the readers do not have wireless or cellular connectivity capabilities.

To illustrate advantageous customization options with one non-limiting example, an administrator in a physician's office can select data categories A, B, and C and configure the reader devices within the office to transmit a report including data corresponding to categories A, B, and C, whereas an administrator in an acute care center can select data categories A, B, D, and E and configure the reader devices within the center to transmit a report including data corresponding to categories A, B, D, and E. The ability to customize reports can significantly reduce administrative and recordkeeping time. The obtained data can also comply with applicable compliance standards more often because opportunities to introduce human error in the reports are reduced.

FIG. 6 illustrates example display text that can be presented to an operator of an assay reader device. As described above, embodiments of the systems and methods described herein can allow the end-user to customize, on a particular assay reader device, the types of information that will be stored in association with test results, significantly increasing compliance and traceability of test results, and reducing transcription and documentation errors. In embodiments including wireless or cellular connectivity capabilities, customized reports including test results associated with selected information categories can be automatically transmitted to a remote server. The top display in the first column of the example displays in FIG. 6 illustrates a display of the assay reader device prompting the user to scan a configuration barcode in order to enable a particular type of information to be associated with test results, or to disable the particular type of information from being associated with the test results. In this non-limiting example, after reading the "SCAN CONFIG BARCODE" prompt, the user scans a barcode that instructs the assay reader device to enable an operator ID function (if the user wishes to associate and store operator ID information with test results), or the user scans a barcode that instructs the assay reader device to disable a operator ID function (if the user does not wish to associate and store operator ID information with test results). After the user scans the barcode indicating the user's selection, the assay reader device displays text confirming the user's selection. In this non-limiting example, the assay reader device displays "OPERATOR ID SCAN ENABLED" or "OPERATOR ID SCAN DISABLED" to the user. The assay reader device may then ask the user to enable or disable other types of information functions, such as but not limited to specimen ID and kit lot ID (see example display tests in FIG. 6 for instance).

In cases where the operator ID function is enabled, the assay reader device will now prompt the user to scan a barcode associated with an operator ID for each test event. For example, prior to prompting the user to input an assay test strip into the device for analysis, the assay reader device will display "SCAN OPERATOR ID" to the user, instructing the user to scan a barcode associated with the user's operator ID. The assay reader device can sequentially query the user to input particular types of information according to the previously-selected, customized configuration settings of the assay reader device. For example, after the user scans a barcode associated with an operator ID, the assay reader device can next prompt the user to scan a barcode associated with a specimen ID for the test event (see, for example, "SCAN SPECIMEN ID" display in FIG. 6), if the device was configured to request specimen ID information. In some cases, the assay reader device will not prompt the user to input an assay test strip for analysis until all information required by the particular configuration settings has been entered. In some cases, the assay reader device can display a summary of the configuration settings (see, for instance, the example display at the top of the middle column in FIG. 6).

A customizable reporting function can be handled at the server side or by one or more remote computing devices that are physically separate from the reader devices but receive information from the reader devices. For example, test result data and associated information from scanned barcodes can be stored in a database of one or more remote computing devices, for example a server system, and the remote computing device can produce customized reports with only fields of interest to the end user. An end user can include but is not limited to a user of the reader device, an administrator in a healthcare facility using the reader device, an entity managing remote server systems, and a public health organization.

Non-compliant test results (for example, having blank fields for any information required by the healthcare group internal standards or applicable regulations) can be flagged in the database. In some examples, statistical analysis can be performed on non-compliant results to identify common sources of non-compliance, such as but not limited to non-compliant test results issuing from a particular batch or lot of test strips, non-complaint information transmitted with test results by a particular healthcare provider or testing location, and non-compliance with reporting frequency or some other deficiency. Such information can be provided automatically in some embodiments to a healthcare organization administrator to assist in developing plans for increased adherence to compliance standards. Compliance with specified information type requirements can facilitate more meaningful statistical analysis of compliant test results by standardizing the information collected from a number of different operators, facilities, or healthcare groups, for example in order to identify and track infectious disease trends for developing disease management plans.

Barcode and connectivity module 110 also includes a barcode reader 112 as described above and additionally a connectivity device, represented graphically by connectivity marker 114. The connectivity device can be a wireless communication device, such as a cellular modem, for accessing a publicly provided, publicly maintained data network. The publicly provided network could be a public telephone network, a public cellular network, or another suitable kind of publicly available data network. Barcode and connectivity module 110 can further include mechanical features for lockingly engaging corresponding features within the bay 132 of the base assay reader device 130 and electronic features for establishing electronic data communications with components of the base assay reader device 130. This can reduce administrative burden and overhead, as well as help reduce or minimize errors associated with manual results documentation and recording.

Though not illustrated, barcode and connectivity module 110 can include an information element as described above. The information element can function to identify the barcode scanning and network connectivity capabilities of barcode and connectivity module 110 to the assay reader device and/or to authenticate the barcode and connectivity module 110 as a module from a specific source or manufacturer.

The barcode and connectivity module 110 can provide all of the functionality and benefits of the barcode module 120 and additionally provide cellular or other wireless connectivity. Such connectivity can be used to document test results across multiple sites and integrate with an electronic medical record (EMR) HIS, LIS, and/or other health record database. For example, in some embodiments test results can be sent to a centralized, server-based database and then routed to the appropriate medical record, hospital, or laboratory database. The automatic transmission of test results can ensure automated documentation of the results to patient records. In addition, automatic transmission of test results can provide real-time alerts to designated medical personnel, for example a doctor of the patient, of potentially dangerous health conditions of the patient, enabling rapid diagnosis and treatment. Further, automatic transmission of test results to public health organizations can enable real-time aggregation and analytics of test result data to identify and possibly curb infectious disease trends. Such medical information transmission can be accomplished via a secure end-to-end connection complying with HIPAA, HITECH, ISO 27001:2013 cybersecurity guidelines, or other industry standards, and data may be encrypted prior to transmission. Cellular or satellite connectivity can enable for rapid transmission of test results from locations even outside of standard clinical settings.

Cartridge 140 can secure an assay 144 for proper alignment within the base assay reader 130. As illustrated, cartridge 140 can include a window for exposing a test region of the assay 144. The assay 144 can be an immunoassay, for example implementing colloidal metal particle technology to furnish sensitivity and strong test performance. The assay 144 can alternatively be a bioassay, ligand binding assay, or any other type of diagnostic test that can be optically imaged to determine a test result. Cartridge 140 can also include a barcode 142 for providing test information, for example a type of test, that can be used in some embodiments to configure an automated process run by the device 130 for determining a result of the assay. The user can scan the barcode 142 of the cartridge 140 using the barcode scanner of a module lockingly engaged with the base assay reader 130, such as the barcode scanner of barcode module 120 or barcode and connectivity module 110, as a way to input information into the base assay reader device 130. Such information can include one or more of patient and/or physician identification information, information relating to the assay test, a barcode password for unlocking functions of the base assay reader device 130, and the like.

The base assay reader device 130 can include one or more additional data communications ports (not illustrated), for example a USB port. The port can be set up as a general purpose hardware interface for the base assay reader device 130. Using this interface, the base assay reader device 130 can support external peripherals, for example a printer or a keyboard. The port can enable the base assay reader device to be connected to a PC for data download. For example, when the base assay reader device is connected to a PC via a USB interface, the reader device can function like a USB drive. In addition, the end user can update the reader device firmware by connecting a USB drive containing the latest firmware revisions to the USB port. Furthermore, the USB port offers a convenient way to upload assay calibration data into the reader device, for example lot specific calibration data.

Though not illustrated, additional module options can be available, for example a connectivity module without barcode features, a wired connection module, and modules having power storage features for increasing device battery life, to name a few examples. In some embodiments the module can be or include a printer. In some embodiments, a module can be or include a separate detection unit. Such a detection unit module may be used to run the same or a different type of test than the base assay reader device 130. In some embodiments the module can be an incubator for incubating the assay before determining a test result. For example, for lateral flow assays, an incubator module may be used to hold the assay and track the development time before providing a reminder or indication to the user to remove the cartridge and insert it into the base assay reader device 130 for reading. For molecular assays, the incubator module may be used for sample preparation and incubation.

Figure 2:
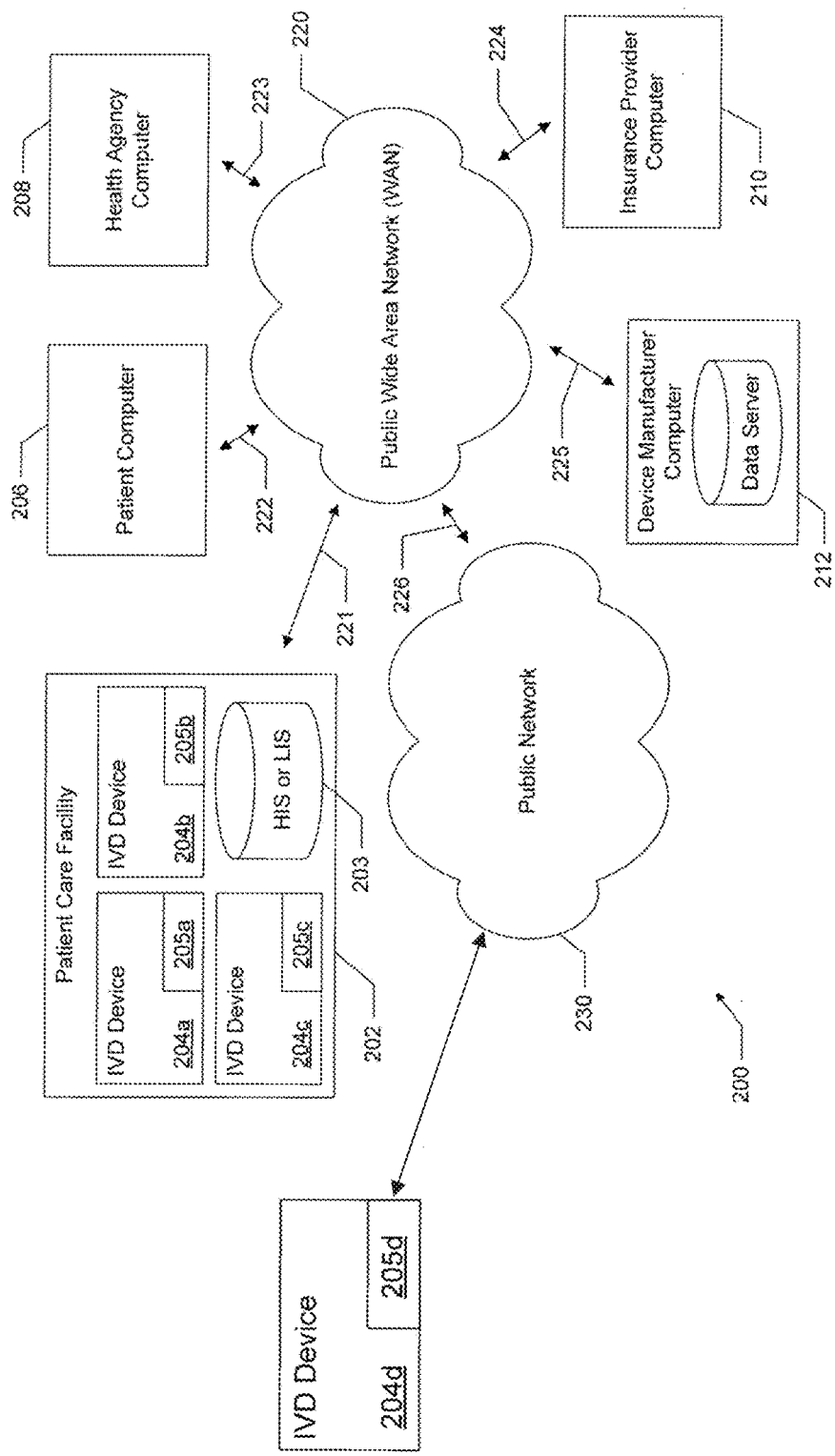
FIG. 2 illustrates a schematic block diagram of an example data network including the disclosed assay reader systems.

Referring now to FIG. 2, a schematic illustration of one networked embodiment of a system 200 is illustrated. In the illustrated embodiment, arrows between certain devices and either the Public Wide Area Network (WAN) 220 or the Public Network 230 indicate that such devices are configured to engage in two-way communication via such a network. For example, if a network element illustrated in FIG. 2 is associated with an arrow pointing to the network element and the Public Network 230, that device is configured to both send data to another device via the Public Network 230 and to receive data from another device via the Public Network 230.

FIG. 2 illustrates an example schematic representation of a patient care facility 202. The patient care facility 202 can represent a patient facility, such as a hospital, doctor's office, or clinic, at which one or more diagnostic tests is applied or given to a patient. In the illustrated embodiment, the patient care facility 202 is shown as including or encompassing a Hospital Information System (HIS) or Laboratory information System (LIS) database 203. That is, in the illustrated embodiment, the patient care facility 202 maintains or otherwise provides access to an HIS or LIS database 203. In the illustrated embodiment, the HIS or LIS database 203 is a repository for test results, summary reports, or other data related to patients utilizing the patient care facility 202. In various embodiments, the HIS or LIS database 203 is additionally coupled with one or more processors (not shown) for performing certain processing tasks, such as analysis of data stored in the HIS or LIS database 203.

In the illustrated embodiment, the patient care facility 202 also includes a plurality of in-vitro diagnostic (IVD) devices 204a, 204b, and 204c. However, as illustrated by IVD device 204d, the network environment 200 can also include IVD devices outside of the patient care facility setting. In one embodiment, the IVD devices are diagnostic test devices, such as devices configured for optically imaging lateral flow assay test strips having an applied biological sample and determining diagnostic test result information based on image data representing the test strips. It should be appreciated that any suitable IVD device could be advantageously used concurrently with the disclosed system.

As further illustrated in FIG. 2, each IVD device 204a, 204b, 204c, and 204d can include a network communication device 205a, 205b, 205c, or 205d, respectively. For example, the network communication devices 205a, 205b, 205c, and 205d can be provided through an insertable accessory module including a cellular modem or another transceiver device configured to communicate with a public network such as the Public Wide Area Network 220 or the Public Network 230. In one embodiment, the network communication devices 205a, 205b, 205c, and 205d enable the respective IVD devices to communicate with either one another, or with another network element, as disclosed herein. In addition, in one embodiment, the network communication devices 205a, 205b, 205c, and 205d enable the respective IVD devices to communicate data indicative of diagnostic test results to remote resources, such as the HIS or LIS database 203 for storage and/or further analysis. Though not illustrated, some IVD devices may be equipped with a barcode scanner module, such as barcode module 120, without network connectivity. Results stored by such devices can be uploaded to one or more of the HIS/LIS, patient computer, or another computing device, for example via a USB connection and appropriately scanned barcode password, for transmission through the networks 230, 220.

The system 200 of FIG. 2 indicates, by arrow 221, that the patient care facility 202 (and the IVD devices/HIS or LIS database contained therein) are configured to communicate via Public Wide Area Network 220. In one embodiment, one or more of the Public Wide Area Network 220 and the Public Network 230 limits, at least in part, access to the network. Moreover, in one embodiment, the disclosed system 200 enables communication between the patient care facility by encrypted or other secure data transmission protocols, as described herein.

System 200 also includes a patient computer 206, health agency computer 208, insurance provider computer 210, and device manufacturer computer 212. Each of these network elements are able to communicate with one another and with the patient care facility 202 via the Public Wide Area Network 220, as indicated by arrows 222, 223, 224, and 225, respectively. Arrow 226 indicates that the Public Wide Area Network 220 can communicate with a Public Network 220 of another type, such as the Internet. Thus, the devices illustrated in FIG. 2 are configured to communicate with one another either via Public Wide Area Network 220, Public Network 230, or some combination thereof.

In the illustrated embodiment, each of the computers enables a different party to communicate with the device manufacturer computer 212 and the IVD devices 204a, 204b, 204c and HIS or LIS database 203. For example, the patient computer 206 enables patients to communicate with the device manufacturer computer 212, the health agency computer 208 enables one or more health agencies to communicate with the patient care facility 202, the insurance provider computer 210 enables an insurance provider to communicate with the patient care facility 202, and the device manufacturer computer 212 enables the manufacturer of the IVD devices to communicate with the patient care facility 202. The device manufacturer computer 212 can enable the IVD devices 204a, 204b, 204c, and 204d to communicate with a data server 212a coupled to the device manufacturer computer 212 to, among other things, receive necessary data, such as calibration data, firmware, or other software and data upgrades, when the need arises.

In various embodiments, the system 200 enables the transmission and exchange of data including test results and additional data sent along with the test results. For example, the data transmitted among the various network elements of the system 200 could include diagnostic data and information, network information, hardware information, and environmental information as described above. In one embodiment, some or all of the data transmitted among the various elements of the illustrated system 200 are encrypted to prevent unwanted access to the transmitted data. In addition to protecting the data from interception and unwanted consumption, this encryption may also validate or maintain the integrity of the transmitted data, such as by providing a checksum or other mechanism to ensure that all transmitted data was received.

In one embodiment, the patient computer 206, health agency computer 208, insurance provider computer 210, and device manufacturer computer 212 are standard desktop or laptop computers accessible by the appropriate party. In another embodiment, one or more of the patient computer 206, health agency computer 208, insurance provider computer 210, and device manufacturer computer 212 are mainframe or server computers configured to handle large quantities of data and/or to provide complex processing and analysis routines. In this embodiment, the appropriate entity which is responsible for the illustrated computer device (e.g., the insurance company responsible for the insurance provider computer) can access some or all of the data uploaded from the IVD devices and stored within the system, depending on the purpose of the user's access. In another embodiment, one or more of the patient computer 206, health agency computer 208, insurance provider computer 210, and device manufacturer computer 212 are portable computers, such as personal digital assistants (PDAs) or cellular telephones, which are configured to enable users to access data from a handheld, portable device. In one embodiment, not shown, one or more medical professionals such as health care personnel staffing the patient care facility 202 access data communicated by the IVD devices 204a, 204b, 204c, and 204d using an appropriate handheld device, such as a PDA, cellular telephone, or other handheld, portable device. In this embodiment, appropriate health care personnel can have access to, or be actively made aware of, patient data immediately upon the patient sample being analyzed by a diagnostic test using an IVD device. It should be appreciated that in various embodiments, entities other than those of the illustrated network elements in FIG. 2 may be able to access the data uploaded by the IVD devices as necessary to perform those entities' respective tasks.

In one embodiment, as discussed above, an IVD device is configured to upload data to one or more database servers. The database servers may be configured to archive test results, aggregate test results into summary reports, or analyze test results for spatial, temporal, or other correlations. These database servers may additionally be configured to perform other analyses on the data, as appropriate, depending upon the type of data uploaded and the goals of the parties managing and implementing the database servers. The ability of IVD devices to upload data directly to database servers via the disclosed connectivity modules results in a number of advantages of the disclosed system. First, patient care facilities can obtain test results from database servers through secure Internet or other network connections and store the retrieved results in their own databases (e.g., their own HIS or LIS databases). In addition, the aggregated test reports available due to the processing of the database servers are of value to public health agencies like the CDC, FDA, and WHO. Such reports can be provided in real-time due to the ability of the disclosed IVD devices to directly and automatically communicate diagnostic test result data to database servers.

Figure 3:
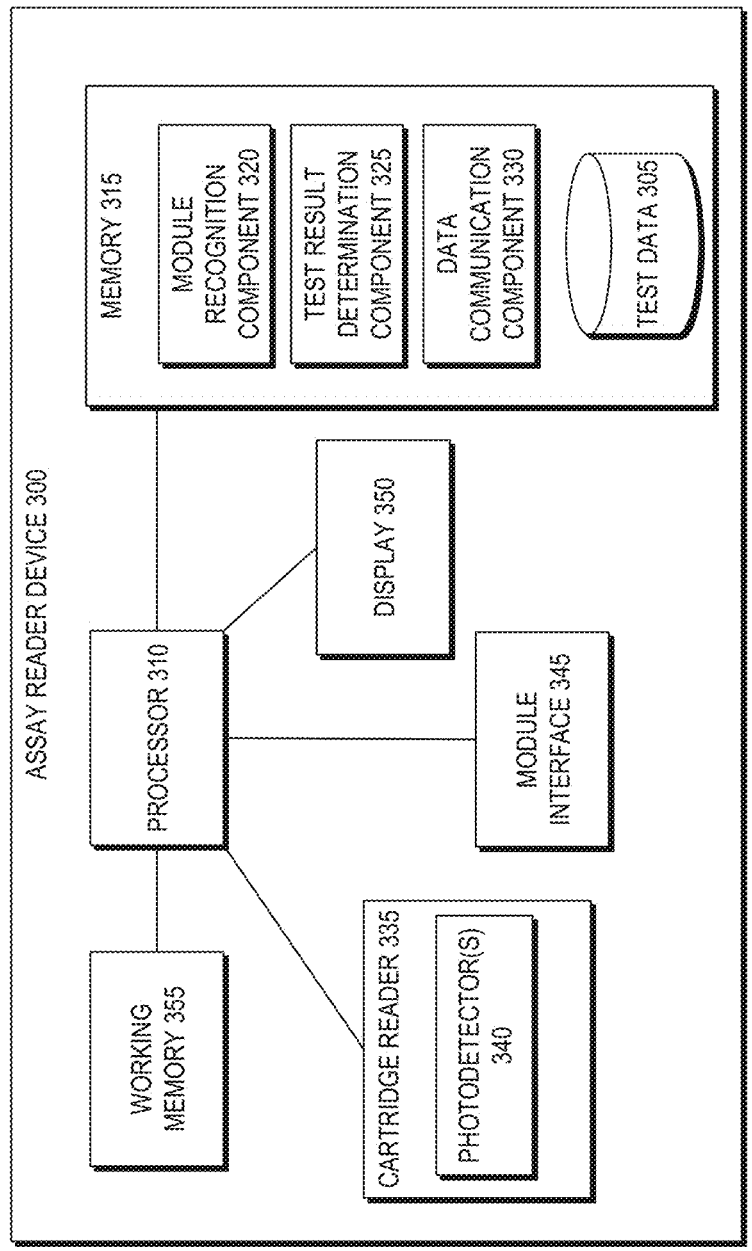
FIG. 3 illustrates a schematic block diagram of an example assay reader device.

FIG. 3 illustrates a schematic block diagram of one possible embodiment of internal components of an example assay reader device 300. The components can include a processor 310 linked to and in electronic communication with a memory 315, working memory 355, cartridge reader 335, module interface 345, and display 350.

Module interface 345 can include circuitry for reading information from an information element of an inserted module and transferring that information to processor 310 for analysis or validation. Thus, module interface 345 can provide a first signal path usable by device 300 for identifying characteristics of a connected module, the characteristics indicative of presence of a barcode scanner in the connected module and connectivity capabilities of the connected module. Module interface 345 can also include a path for establishing electronic communications with the barcode reader, network transceiver, power supply, or other electronic components of an inserted module. Thus, module interface 345 can provide a second signal path configured to receive barcode data from the connected module, the barcode data representing a barcode imaged by the connected module and/or information or instructions represented by the barcode.

The cartridge reader 335 can include one or more photodetectors 340 for reading an assay held in an inserted cartridge and optionally any information on the inserted cartridge, for example a barcode printed on the cartridge. The cartridge reader 335 can send image data from the one or more photodetectors to the processor 310 for analysis of the image data representing the imaged assay to determine a test result of the assay. The cartridge reader 335 can further send image data from the one or more photodetectors representing the imaged cartridge for use in determining which one of a number of automated operating processes to implement for imaging the assay and/or analyzing the image data of the assay. The photodetector(s) 340 can be any device suitable for generating electric signals representing incident light, for example a PIN diode or array of PIN diodes, a charge-coupled device (CCD), or a complementary metal oxide semiconductor (CMOS) sensor, to name a few examples. The cartridge reader 335 can also include a component for detecting cartridge insertion, for example a mechanical button, electromagnetic sensor, or other cartridge sensing device. An indication from this component can instruct the processor 310 to begin an automated assay reading process without any further input or instructions from the user of the device 300.

Processor 310 can be configured to perform various processing operations on image data received from the cartridge reader 335 and/or module interface 345 in order to determine and store test result data, as will be described in more detail below. Processor 310 may be a general purpose processing unit implementing assay analysis functions or a processor specially designed for assay imaging and analysis applications. The processor 310 can be a microcontroller, a microprocessor, or ASIC, to name a few examples, and may comprise a plurality of processors in some embodiments.

As shown, the processor 310 is connected to a memory 315 and a working memory 355. In the illustrated embodiment, the memory 315 stores module recognition component 320, test result determination component 325, data communication component 330, and test data repository 305. These modules include instructions that configure the processor 310 of device 300 to perform various module interfacing, image processing, and device management tasks. Working memory 355 may be used by processor 310 to store a working set of processor instructions contained in the modules of memory 315. Alternatively, working memory 355 may also be used by processor 310 to store dynamic data created during the operation of device 300.

As mentioned above, the processor 310 may be configured by several modules stored in the memory 315. The module recognition component 320 may include instructions that control the electronic communications between the processor and the module interface 345. For example, module recognition component 320 may include instructions that call subroutines to configure the processor 310 to read an information element of an inserted module to authenticate the module as compatible with the device 300 and determine capabilities of the inserted module. The test result determination component 325 can include instructions that call subrooutines to configure the processor 310 to analyze assay image data received from the photodetector(s) 340 to determine a result of the assay. For example, the processor can compare image data to a number of templates or pre-identified patterns to determine the test result. In some implementations, test result determination component 325 can configure the processor 310 to implement adaptive read processes on image data from the photodetector(s) 340 to improve specificity of test results and to reduce false-positive results by compensating for background and non-specific binding.

The data communication component 330 can determine whether a module has been inserted into the device that enables wireless data transmission and can manage transmission of test result data to determined personnel and/or remote databases. For example, test result data transmission can be based on barcode data received together with the assay image, where the assay image is used to generate the test result and is stored in association with the test result, and wherein the barcode data is further stored in association with the test result. If the device 300 is not coupled with a network-communication-enabled module, the data communication component 330 can cause local storage of test results and associated information in the test data repository 305. If a local wired or wireless connection is established between the device 300 and another computing device, for example a hospital, clinician, or patient computer, the data communication component 330 can prompt a user of the device 300 to scan a password barcode using an inserted module in order to access the data in the repository 305.

The processor 310 can be configured to control the display 350 to display captured image data, imaged barcodes, test results, and user instructions, for example. The display 350 may include a panel display, for example, a LCD screen, LED screen, or other display technologies, and may implement touch sensitive technologies.

Processor 310 may write data to data repository 305, for example data representing captured images of barcodes and assays, instructions or information associated with imaged barcodes, and determined test results. While data repository 305 is represented graphically as a traditional disk device, those with skill in the art would understand that the data repository 305 may be configured as any storage media device. For example, data repository 305 may include a disk drive, such as a hard disk drive, optical disk drive or magneto-optical disk drive, or a solid state memory such as a FLASH memory, RAM, ROM, and/or EEPROM. The data repository 305 can also include multiple memory units, and any one of the memory units may be configured to be within the assay reader device 300, or may be external to the device 300. For example, the data repository 305 may include a ROM memory containing system program instructions stored within the assay reader device 300. The data repository 305 may also include memory cards or high speed memories configured to store captured images which may be removable from the device 300.

Although FIG. 3 depicts a device having separate components to include a processor, cartridge reader, module interface, and memory, one skilled in the art would recognize that these separate components may be combined in a variety of ways to achieve particular design objectives. For example, in an alternative embodiment, the memory components may be combined with processor components to save cost and improve performance.

Additionally, although FIG. 3 illustrates a number of memory components, including memory 315 comprising several modules and a separate memory 355 comprising a working memory, one of skill in the art would recognize several embodiments utilizing different memory architectures. For example, a design may utilize ROM or static RAM memory for the storage of processor instructions implementing the modules contained in memory 315. The processor instructions may be loaded into RAM to facilitate execution by the processor 310. For example, working memory 355 may comprise RAM memory, with instructions loaded into working memory 355 before execution by the processor 310.

Figure 4:
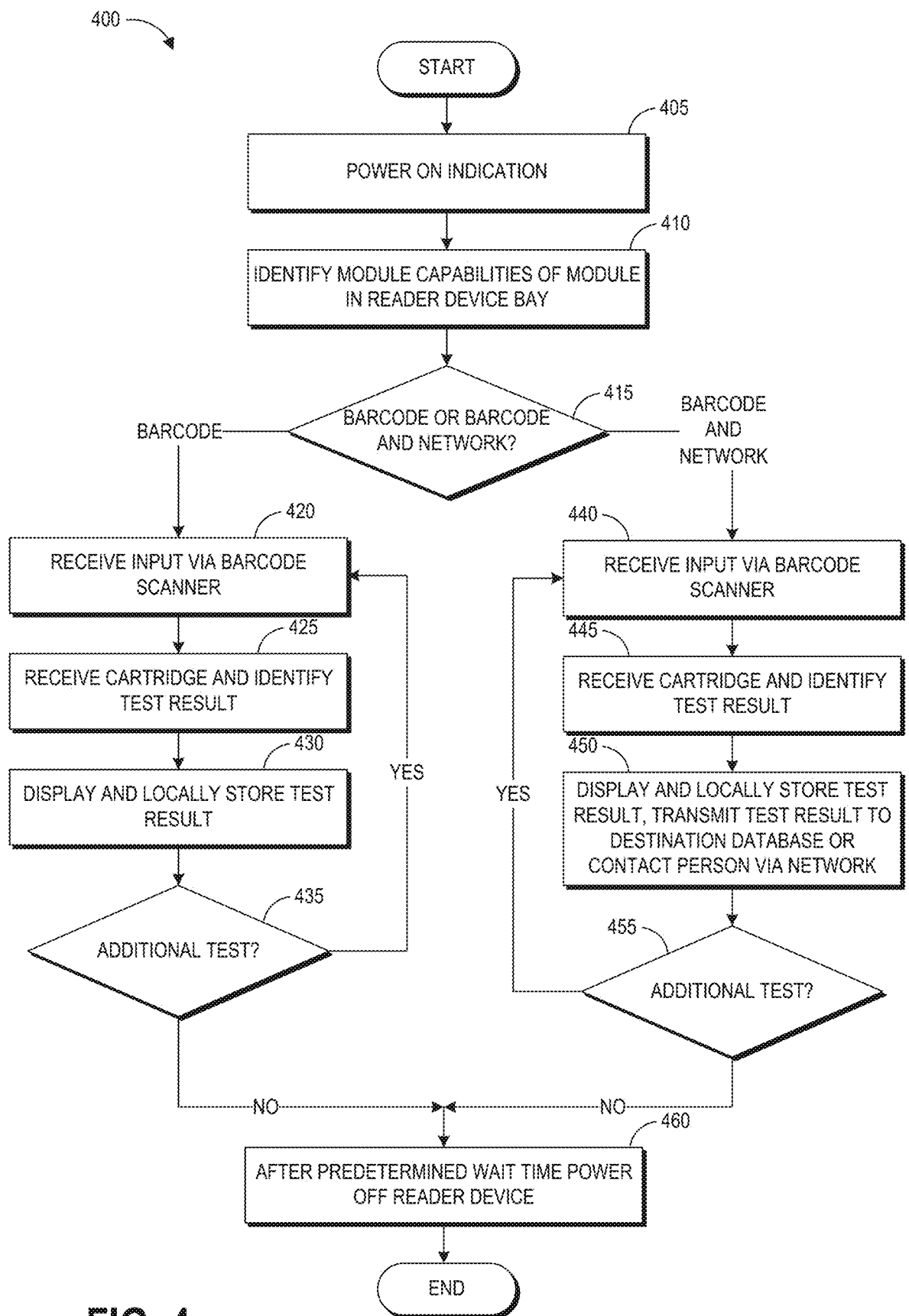
FIG. 4 is a flowchart depicting an example operations process of an assay reader device as disclosed herein.

FIG. 4 is a flowchart depicting an example operations process 400 of an assay reader device as disclosed herein. The process 400 can be implemented by an assay reader device 130 and/or processor 310 in some embodiments.

At block 405, the processor 310 can receive a power on indication, for example in response to a user pressing a single button located on an assay reader device.

At block 410, the processor can identify whether a module is inserted into a bay of the assay reader device and, if so, can identify the capabilities of the inserted module. As described above, these capabilities can include one or more of barcode scanning and network connectivity including cellular or satellite network connectivity.

At decision block 415, the processor 310 can identify whether the inserted module capabilities include barcode scanning or barcode scanning and network connectivity.

If the inserted module capabilities include barcode scanning, the process 400 can transition to block 420 to receive input via a barcode scanner of the inserted module. Such input can include information for storage in association with test results and/or information that configures the operations of the assay reader device, for example instructions regarding imaging procedures for acquiring image data of an inserted assay. In some embodiments device operation can be configured via a pattern of button presses as described above. At block 425, the process 400 can include receiving an assay test holding cartridge in a receiving aperture within the assay reader device, imaging the assay, and determining a test result based on the image data representing the assay. Block 425 can be implemented as any of the disclosed reader operation modes, such as but not limited to an end-point read mode or a walkaway mode. At block 430 the processor 310 can display and locally store the test result and any associated data.

At decision block 435 the processor can determine whether an additional test is to be performed, for example by receiving an indication that an additional barcode has been scanned (by looping back to block 420) or that an additional cartridge has been inserted (by looping back to block 425). In such instances the process can loop back through blocks 420-430, in the order shown or with blocks 420 and 425 switched.

If the inserted module capabilities include barcode scanning and network connectivity, the process 400 can transition to block 440 to receive input via a barcode scanner of the inserted module. Such input can include information for storage in association with test results and/or information that configures the operations of the assay reader device, for example instructions regarding imaging procedures for acquiring image data of an inserted assay or instructions regarding where test result data should be transmitted. In some embodiments device operation can be configured via a pattern of button presses as described above. At block 445, the process 400 can include receiving an assay test holding cartridge in a receiving aperture within the assay reader device, imaging the assay, and determining a test result based on the image data representing the assay. Block 445 can be implemented as any of the disclosed reader operation modes, for example an end-point read mode or a walkaway mode.

At block 450 the processor 310 can display and locally store the test result together with any associated data, for example an image of the assay used to generate the test result and additional information provided via a scanned barcode. Additionally or alternatively, the processor 310 can display and transmit the test result and optionally any associated data to a destination database or contact person via a network. For example, this can be accomplished through the connectivity module 110 inserted to and in electronic communication with base assay reader device 130 in some embodiments.

At decision block 455 the processor can determine whether an additional test is to be performed, for example by receiving an indication that an additional barcode has been scanned (by looping back to block 440) or that an additional cartridge has been inserted (by looping back to block 445). In such instances the process can loop back through blocks 440-450, in the order shown or with blocks 440 and 445 switched.

If, at either of blocks 435 or 455, the processor 310 determines that no additional test is to be performed (for example by inactivity of any of the sensors of the assay reader device), then the process 300 can transition to block 460. At block 460 the processor 310 can wait for a predetermined time period before powering off the assay reader device.

Figure 5A:
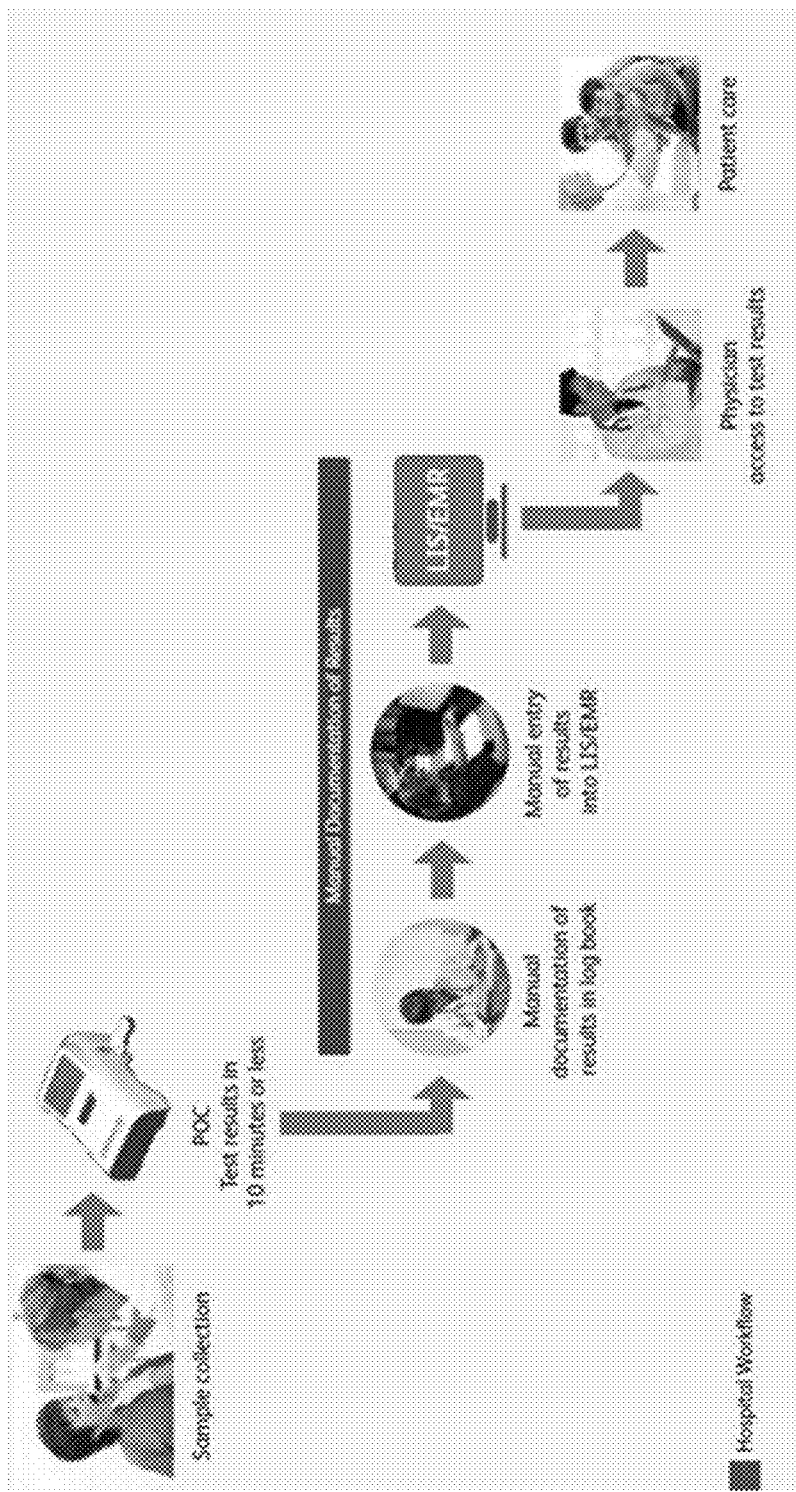
FIG. 5A illustrates an example hospital workflow without a wireless point of care testing solution.

FIG. 5A illustrates an example hospital workflow without a wireless point of care testing solution. As illustrated, a sample is collected and test results are provided at the point of care. Embodiments of a reader device described herein can provide test results in ten minutes or less. Subsequently, in order to provide manual documentation of results, the results are manually documented in a log book and then manually entered into a laboratory information system or electronic medical record. After the results are entered into the laboratory information system or electronic medical record, the physician is able to access the test results and provide patient care. In such a workflow the physician must wait for the manual documentation to be complete before reviewing test results and providing care to the patient.

Figure 5B:
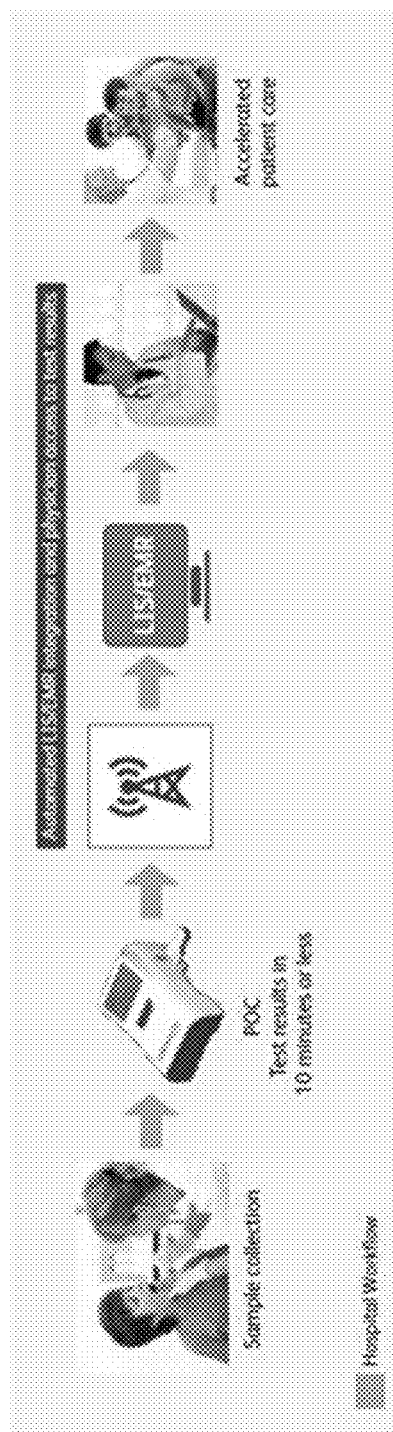
FIG. 5B illustrates an example hospital workflow implementing a streamlined workflow via the disclosed assay reader devices that provide a wireless point of care testing solution.

FIG. 5B illustrates an example hospital workflow implementing a streamlined workflow via the disclosed assay reader devices that provide a wireless point of care testing solution. As illustrated, a sample is collected and test results are provided at the point of care. Embodiments of a reader device including a network-communication-enabled module described herein can provide test results in ten minutes or less. From the point of care, the results are automatically transmitted via a network directly to a laboratory information system or electronic medical record. The transmitted results are immediately available to the physician at the point of care via the laboratory information system or electronic medical record, facilitating accelerated patient care. In this workflow, the physician is able to access the patient's test results while the patient is still in the office rather than having to wait for manual documentation of the test results, thereby enabling more rapid treatment of the patient.

One advantage of the base assay reader devices described herein is that each device can be upgraded at any time, for example by provision of a new module, providing a scalable platform to meet the growing needs of a healthcare group. A base assay reader device can incorporate other testing platforms and instruments via the module receiving bay. Further, a single assay reader device can be used for multiple functions via interchangeable modules. In one example, a health services provider can purchase and use the base assay reader device without any of the described modules. As the provider expands its capabilities, requires increased functionality, or additional purchasing resources become available, the provider can buy one or more modules as needed to meet its particular needs. The modules can be inserted into the base assay reader devices to quickly and easily expand the functionality of the devices, without any modification to the previously-acquired base assay reader device. As another example, a health services provider can purchase a kit having a base assay reader device and one or more modules, and later a new barcode scanner module may be developed with additional functionality. The provider can purchase the new barcode scanner whenever it wants and still use the previously-acquired base assay reader device with the old module changed out for the new module. In another example, the barcode scanner or some other component in a module may malfunction or break. A spare can be used with the base assay reader device while the first barcode scanner is repaired.

Other advantages of the disclosed base assay reader devices with network connectivity modules is that the single access-point integration with electronic medical records and laboratory information systems provides test results quickly, enabling decision making while the patient is on site. This automated documentation can facilitate accelerated patient care by accelerating physician access to test results, providing the physician with results almost immediately after the test is completed, regardless of testing location. The disclosed base assay reader devices with a barcode scanning module reduce transcription errors compared to systems that require manual entry of identifying information.

Implementing Systems and Terminology

Implementations disclosed herein provide systems, methods and apparatus for a modular, reconfigurable assay reader. One skilled in the art will recognize that these embodiments may be implemented in hardware or a combination of hardware and software and/or firmware.

The assay reader device may include one or more image sensors, one or more image signal processors, and a memory including instructions or modules for carrying out the processes discussed above. The device may also have data, a processor loading instructions and/or data from memory, one or more communication interfaces, one or more input devices, one or more output devices such as a display device and a power source/interface. The device may additionally include a transmitter and a receiver. The transmitter and receiver may be jointly referred to as a transceiver. The transceiver may be coupled to one or more antennas for transmitting and/or receiving wireless signals.

The functions described herein may be stored as one or more instructions on a processor-readable or computer-readable medium. The term "computer-readable medium" refers to any available medium that can be accessed by a computer or processor. By way of example, and not limitation, such a medium may comprise RAM, ROM, EEPROM, flash memory, CD-ROM or other optical disk storage, magnetic disk storage or other magnetic storage devices, or any other medium that can be used to store desired program code in the form of instructions or data structures and that can be accessed by a computer. Disk and disc, as used herein, includes compact disc (CD), laser disc, optical disc, digital versatile disc (DVD), floppy disk and Blu-ray® disc where disks usually reproduce data magnetically, while discs reproduce data optically with lasers. It should be noted that a computer-readable medium may be tangible and non-transitory. The term "computer-program product" refers to a computing device or processor in combination with code or instructions (e.g., a "program") that may be executed, processed or computed by the computing device or processor. As used herein, the term "code" may refer to software, instructions, code or data that is/are executable by a computing device or processor.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, any of the signal processing algorithms described herein may be implemented in analog circuitry. A computing environment can include any type of computer system, including, but not limited to, a computer system based on a microprocessor, a mainframe computer, a digital signal processor, a portable computing device, a personal organizer, a device controller, and a computational engine within an appliance, to name a few.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component or directly connected to the second component. As used herein, the term "plurality" denotes two or more. For example, a plurality of components indicates two or more components.

The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like. The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the spirit or scope of the invention. Thus, the present invention is not intended to be limited to the implementations shown herein but is to be accorded the widest scope consistent with the principles and novel features disclosed herein.

What is claimed is:

1. A diagnostic test device comprising:
   an optical sensor configured to generate a signal indicating one or more optical characteristics of an assay following application of a sample to the assay;
   a module interface comprising:
      a bay configured to receive a connected module of a plurality of interchangeable modules, and
      a signal path configured to identify a characteristic of the connected module indicative of connectivity capabilities of the connected module;
   at least one processor; and
   a memory having instructions stored thereon that configure the at least one processor to:
      determine a test result based at least partly on the signal generated by the optical sensor,
      determine the connectivity capabilities of the connected module,
      in response to determining that the connected module has connectivity capabilities with a remote storage device, automatically send the test result to the remote storage device, and
      in response to determining that the connected module does not have connectivity capabilities with a remote storage device, automatically store the test result in the memory.

2. The diagnostic test device of claim 1, further comprising an additional optical sensor positioned to detect additional information on the assay or a cartridge holding the assay, wherein the at least one processor is configured to use the additional information to establish operating parameters of the diagnostic test device.

3. The diagnostic test device of claim 1, further comprising an additional optical sensor positioned to detect additional information on the assay or a cartridge holding the assay, wherein the at least one processor is configured to store the additional information in association with the test result.

4. The diagnostic test device of claim 1, further comprising the connected module.

5. The diagnostic test device of claim 4, wherein the connected module further comprises a barcode scanner.

6. The diagnostic test device of claim 4, wherein the connected module comprises a cellular modem configured to provide the connectivity capabilities.

7. The diagnostic test device of claim 4, wherein the connected module comprises an information element, wherein the at least one processor is configured to retrieve, via the signal path, module information from the information element and determine the connectivity capabilities of the connected module based on the module information.

8. Non-transitory computer-readable media configured with computer-executable instructions that, when executed, cause a hardware processor to:
   determine connectivity capabilities of a connected module inserted into a bay of an assay reader device;
   receive assay image data from an assay reading image sensor of the assay reader device, the assay image data representing one or more optical characteristics of an assay inserted into or positioned adjacent to the assay reader device;

determine a test result based at least partly on analyzing the assay image data;

in response to determining that the connected module has connectivity capabilities with a remote storage device physically separated from the assay reader device, automatically send the test result to the remote storage device; and in response to determining that the connected module does not have connectivity capabilities with a remote storage device, automatically store the test result in a memory of the assay reader device.

9. The non-transitory computer-readable media of claim 8, further having stored thereon instructions that, when executed, cause the hardware processor to:

determine presence of a barcode scanner in the connected module;

receive barcode image data from the connected module representing at least one barcode;

identify, based on analysis of the barcode image data, the at least one barcode as an instruction barcode; and retrieve instructions associated with the instruction barcode.

10. The non-transitory computer-readable media of claim 9, further having stored thereon instructions that, when executed, cause the hardware processor to determine the test result based at least partly on the instructions associated with the instruction barcode.

11. The non-transitory computer-readable media of claim 9, further having stored thereon instructions that, when executed, cause the hardware processor to instruct the assay reading image sensor to obtain the assay image data at a predetermined timing after insertion of the assay into the assay reader device based at least partly on the instructions associated with the instruction barcode.

12. The non-transitory computer-readable media of claim 8, further having stored thereon instructions that, when executed, cause the hardware processor to:

determine presence of a barcode scanner in the connected module;

receive barcode image data from the connected module representing at least one barcode;

identify, based on analysis of the barcode image data, the at least one barcode as an identification barcode;

determine information represented by the identification barcode;

in response to determining that the connected module has connectivity capabilities with a remote storage device physically separated from the assay reader device, automatically send the information represented by the identification barcode with the test result to the remote storage device; and in response to determining that the connected module does not have connectivity capabilities with a remote storage device, automatically store the information represented by the identification barcode with the test result in a memory of the assay reader device.

13. A diagnostic testing process comprising, by one or more hardware processors:

determine connectivity capabilities of a connected module inserted into a bay of an assay reader device;

receiving assay image data from an assay reading image sensor of the assay reader device, the assay image data representing one or more optical characteristics of an assay inserted into or positioned adjacent to the assay reader device;

determining a test result based at least partly on analyzing the assay image data;

in response to determining that the connected module has connectivity capabilities with a remote storage device physically separated from the assay reader device, automatically sending the test result to the remote storage device; and in response to determining that the connected module does not have connectivity capabilities with a remote storage device, automatically storing the test result in a memory of the assay reader device.

14. The process of claim 13, further comprising:

determining presence of a barcode scanner in the connected module;

receiving barcode image data from the connected module representing at least one barcode;

identifying, based on analysis of the barcode image data, the at least one barcode as an instruction barcode; and retrieving instructions associated with the instruction barcode.

15. The process of claim 14, further comprising determining the test result based at least partly on the instructions.

16. The process of claim 14, further comprising instructing the assay reading image sensor to obtain the assay image data at a predetermined timing after insertion of the assay into the assay reader device based at least partly on the instructions.

17. The process of claim 13, further comprising:

determining presence of a barcode scanner in the connected module;

receiving barcode image data from the connected module representing at least one barcode;

identifying, based on analysis of the barcode image data, the at least one barcode as an identification barcode; and determining information represented by the identification barcode.

18. The process of claim 17, further comprising:

in response to determining that the connected module has connectivity capabilities with a remote storage device physically separated from the assay reader device, automatically sending the information represented by the identification barcode with the test result to the remote storage device; and in response to determining that the connected module does not have connectivity capabilities with a remote storage device, automatically storing the information represented by the identification barcode with the test result in a memory of the assay reader device.

19. The process of claim 17, further comprising in response to determining that the connected module has connectivity capabilities with a remote storage device physically separated from the assay reader device, automatically sending instructions to route the test result from the remote storage device to another remote storage device, the another remote storage device identified based on the information represented by the identification barcode.

20. The process of claim 17, further comprising in response to determining that the connected module has connectivity capabilities with a remote storage device physically separated from the assay reader device, automatically sending the test result to the personal computing device of a clinician, the clinician identified based on the information represented by the identification barcode.

* * * * *